(12) United States Patent
Dalvi et al.

(10) Patent No.: US 9,415,008 B2
(45) Date of Patent: *Aug. 16, 2016

(54) DRY POWDER INHALER

(71) Applicant: Teva Branded Pharmaceutical Products R&D, Inc., Frazer, PA (US)

(72) Inventors: Mukul Dalvi, Weston, FL (US); Seah Kee Tee, Weston, FL (US)

(73) Assignee: Teva Branded Pharmaceutical Products R&D, Inc., Frazer, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/001,853

(22) Filed: Jan. 20, 2016

(65) Prior Publication Data

US 2016/0206559 A1 Jul. 21, 2016

Related U.S. Application Data

(60) Provisional application No. 62/105,479, filed on Jan. 20, 2015.

(51) Int. Cl.
| | |
|---|---|
| *A61K 31/56* | (2006.01) |
| *A61M 15/00* | (2006.01) |
| *A61K 9/00* | (2006.01) |
| *A61K 31/137* | (2006.01) |

(52) U.S. Cl.
CPC ............ *A61K 9/0075* (2013.01); *A61K 31/137* (2013.01); *A61K 31/56* (2013.01); *A61M 15/0005* (2014.02); *A61M 15/0021* (2014.02); *A61M 2202/064* (2013.01)

(58) Field of Classification Search
CPC .... A61K 31/569; A61K 31/137; A61K 31/57
USPC ..................................... 514/171; 128/203.15
See application file for complete search history.

(56) References Cited

U.S. PATENT DOCUMENTS

| | | | |
|---|---|---|---|
| 6,395,300 B1 | 5/2002 | Straub | |
| 9,066,957 B2 | 6/2015 | Dalvi | |
| 2002/0078950 A1 | 6/2002 | OLeary | |
| 2002/0088463 A1 | 7/2002 | Keane | |
| 2004/0105821 A1 | 6/2004 | Bernstein | |
| 2005/0042171 A1 | 2/2005 | Gavin | |
| 2013/0064870 A1 | 3/2013 | Bhowmick | |
| 2015/0099726 A1 | 4/2015 | Dalvi | |

FOREIGN PATENT DOCUMENTS

| | | |
|---|---|---|
| WO | 0197889 | 12/2001 |
| WO | 0200281 | 1/2002 |
| WO | 2011054527 | 5/2011 |
| WO | 2011145109 | 11/2011 |

OTHER PUBLICATIONS

Invitation to pay additional fees and, where possible, protect fee mailed Mar. 9, 2015 for International Application No. PCT/US2014/059285.
Nelson, H. S. et al., "Efficacy and safety of fluticasone propionate 44¼g/salmeterol 21¼g administered in a hydrofluoralkane metered-dose inhaler as an initial asthma maintenance treatment," Annals of Allergy, Asthma & Immunology, vol. 91, No. 3, Sep. 1, 2003, pp. 263-269.
Entire patent prosecution history of U.S Appl. No. 14/507,210, filed Oct. 6, 2014, entitled, "Dry Powder Inhaler," now U.S. Pat. No. 9,066,957, issued Jun. 30, 2015.
International Search Report and Written Opinion of the International Searching Authority issued in related International Application No. PCTUS2016/014072 dated Apr. 28, 2016.

*Primary Examiner* — Raymond Henley, III
(74) *Attorney, Agent, or Firm* — RatnerPrestia

(57) ABSTRACT

This invention provides a dry powder inhaler comprising: a dry powder medicament comprising fluticasone propionate, salmeterol xinafoate and a lactose carrier; wherein, the delivered dose of fluticasone propionate per actuation is less than 100 μg; and wherein the dose provides a baseline-adjusted $FEV_1$ in a patient of more than 150 mL within 30 minutes of receiving the dose. A method of treating a patient includes administering to a patient a dry powder medicament having fluticasone propionate, salmeterol xinafoate and a lactose carrier; wherein, the delivered dose of fluticasone propionate per actuation is less than 100 μg; and wherein the dose provides a baseline-adjusted $FEV_1$ in a patient of more than 150 mL within 30 minutes of receiving the dose.

20 Claims, 11 Drawing Sheets

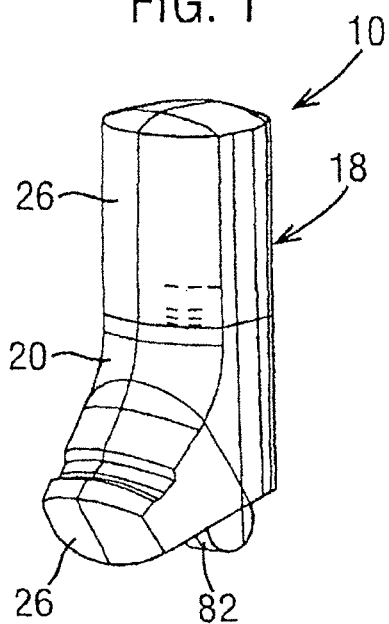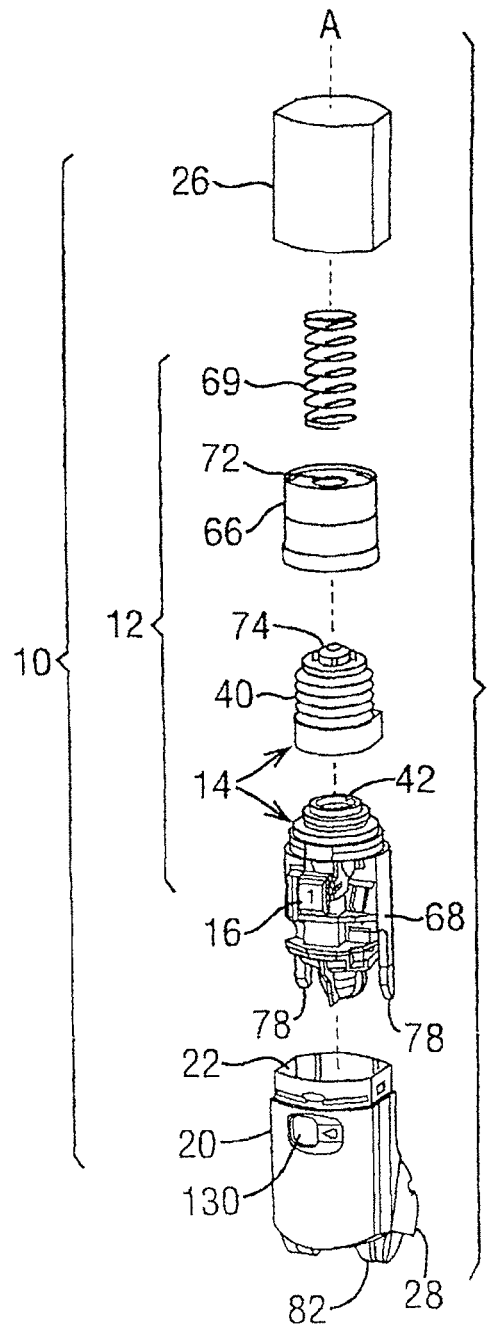

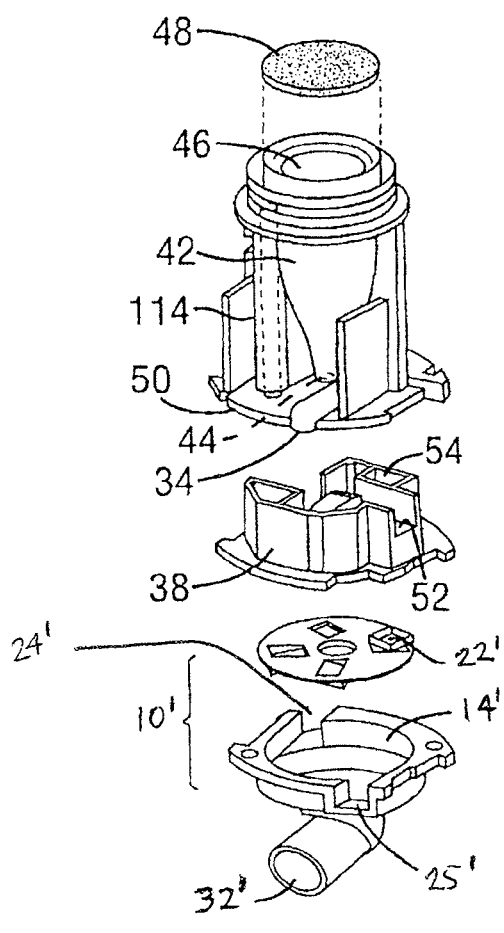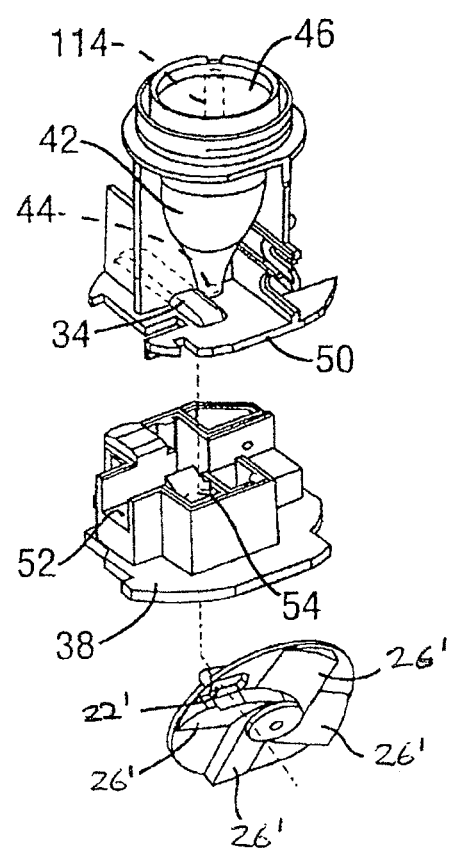

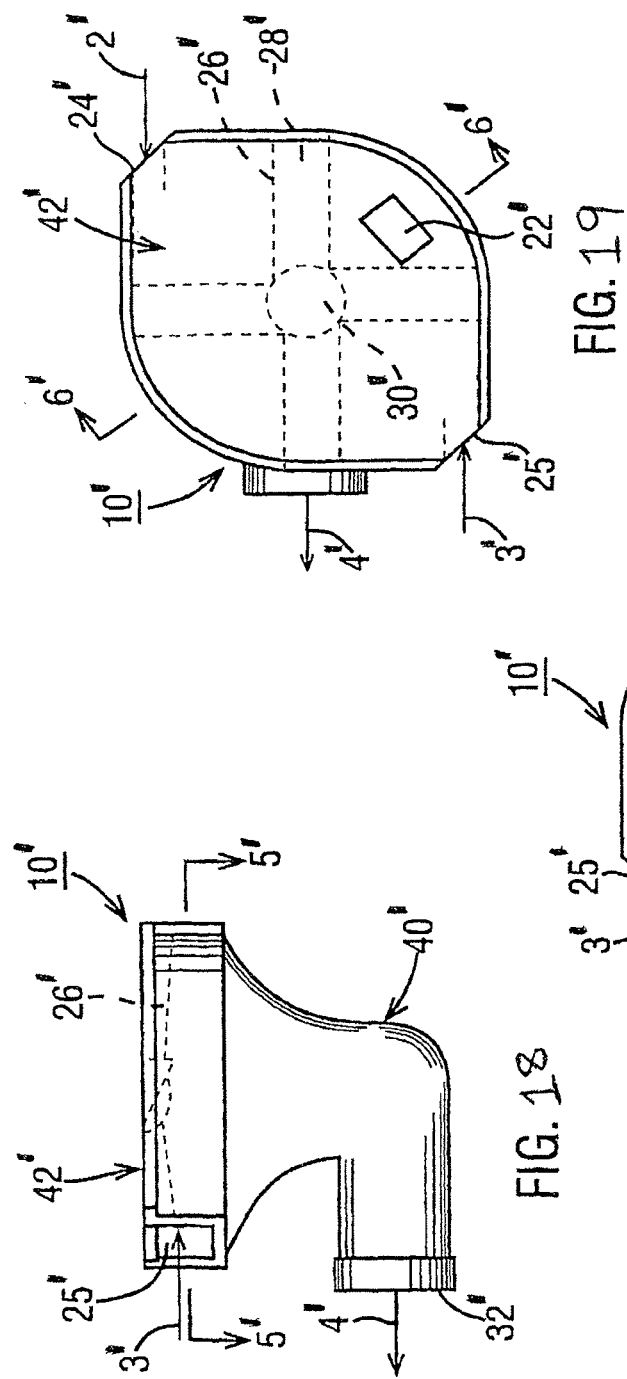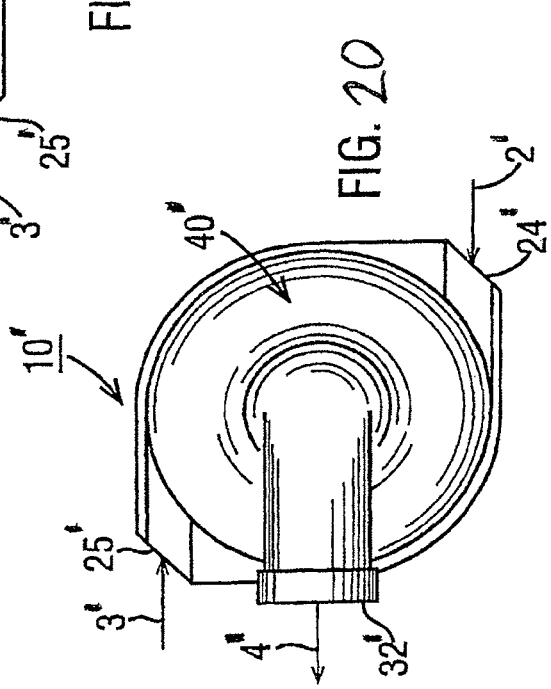
FIG. 19
FIG. 20
FIG. 18

DRY POWDER INHALER

CROSS-REFERENCE TO RELATED APPLICATION

This application claims priority from U.S. Provisional Application No. 62/105,479, filed Jan. 20, 2015, the entire disclosure of which is incorporated herein by reference in its entirety for all purposes.

FIELD OF THE INVENTION

The present invention relates to a dry powder inhaler, and particularly to a dry powder inhaler containing a combination of fluticasone and salmeterol.

BACKGROUND OF THE RELATED ART

Fluticasone propionate is a corticosteroid indicated for the treatment of asthma and allergic rhinitis. It is also used to treat eosinophilic esophagitis. It is named as S-(fluoromethyl)-6α, 9-difluoro-11β,17-dihydroxy-16α-methyl-3-oxoandrosta-1, 4-diene-17β-carbothioate-17-propanoate and has the following structure:

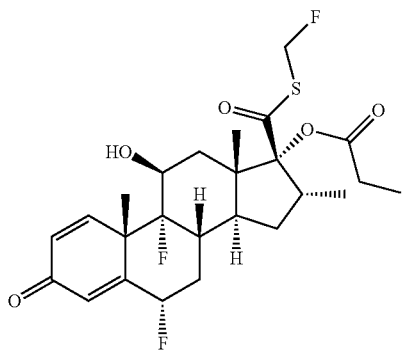

Salmeterol is a long-acting $\beta_2$-adrenergic receptor agonist that is indicated for the treatment of asthma and chronic obstructive pulmonary disease (COPD). It is named as (RS)-2-(hydroxymethyl)-4-{1-hydroxy-2-[6-(4-phenylbutoxy) hexylamino]ethyl}phenol and has the following structure:

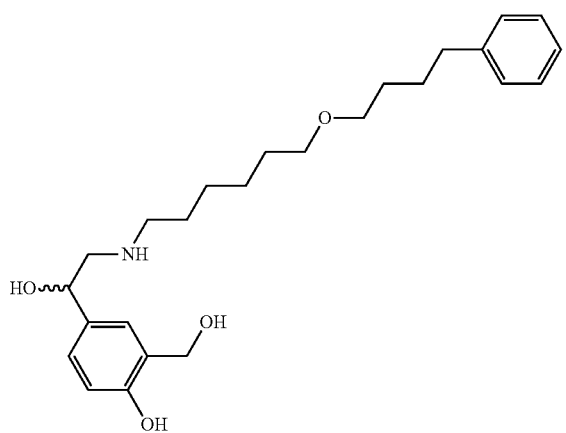 [SMILES: OCc1cc(C(O)CNCCCCCCOCCCCc2ccccc2)ccc1O]

Salmeterol is typically administered as the xinafoate salt, the structure of which is well-known in the art.

The combination of salmeterol (as the xinafoate salt) and fluticasone propionate is marketed in the EU by Allen & Hanburys as Seretide®, using either the Evohaler® pressurised metered-dose inhaler (pMDI) or the Accuhaler® dry powder inhaler (DPI). The Accuhaler® uses blisters filled with a blend of the micronised active agents and lactose monohydrate. It is marketed in three dosage strengths, each providing 50 micrograms of salmeterol xinafoate and 100, 250 or 500 micrograms of fluticasone propionate. In the US, the product is called Advair® and the inhaler is called Diskus®.

Seretide® is indicated in the regular treatment of asthma where use of a combination product (long-acting $\beta_2$-agonist and inhaled corticosteroid) is appropriate. This is where either: patients are not adequately controlled with inhaled corticosteroids and as needed inhaled short acting $\beta_2$-agonist; or patients are already adequately controlled on both inhaled corticosteroid and long-acting $\beta_2$-agonist.

Seretide® is also indicated for the symptomatic treatment of patients with COPD, with a $FEV_1$<60% predicted normal (pre-bronchodilator) and a history of repeated exacerbations, who have significant symptoms despite regular bronchodilator therapy. $FEV_1$ is a measurement used in spirometry which means the forced expiratory volume in one second. This is the amount of air which can be forcibly exhaled from the lungs in the first second of a forced exhalation. The measurement of $FEV_1$ is used by healthcare professionals to determine lung function.

Combination products are well established in the art and are known to improve patient convenience and compliance. A drawback of combination products is that control over the dose of the individual active ingredients is reduced. The primary concern over side effects is in respect of the $\beta_2$-agonist, since the therapeutic window is narrower and $\beta_2$-agonists are associated with serious adverse effects, including cardiac side-effects. However, it is also desirable to reduce the systemic exposure of the inhaled corticosteroids.

Thus, there is a requirement in the art for an improved fluticasone/salmeterol combination product which retains the therapeutic effect of both products, but which reduces the systemic exposure of the fluticasone.

SUMMARY OF THE INVENTION

Accordingly, the present invention provides a dry powder inhaler comprising: a dry powder medicament comprising fluticasone propionate, salmeterol xinafoate and a lactose carrier; wherein, the delivered dose of fluticasone propionate per actuation is less than 100 μg; and wherein the dose provides a baseline-adjusted $FEV_1$ in a patient of more than 150 mL within 30 minutes of receiving the dose.

The present invention also provides a method for the treatment of asthma, allergic rhinitis, or COPD comprising administering to a patient a dry powder medicament according to any embodiment described herein. In one embodiment, the dry powder medicament comprises fluticasone propionate, salmeterol xinafoate and a lactose carrier; wherein, the delivered dose of fluticasone propionate per actuation is less than 100 μg; and wherein the dose provides a baseline-adjusted $FEV_1$ in a patient of more than 150 mL within 30 minutes of receiving the dose. The method of treatment may use any inhaler, including any inhaler as described herein. In one embodiment, the method of treatment provides a dose of fluticasone propionate/salmeterol whereby the fluticasone propionate is less than 75 μg. In other embodiments, the method of treatment provides doses of fluticasone propionate/salmeterol in μg that are 50/12.75 or 25/12.75 per actuation.

DESCRIPTION OF THE FIGURES

FIG. 1 is a first side isometric view of a dry powder inhaler according to a preferred embodiment;

FIG. 2 is an exploded, second side isometric view of the inhaler of FIG. 1;

FIG. 7 is an exploded first side isometric view of a hopper and a deagglomerator of the inhaler of FIG. 1;

FIG. 8 is an exploded second side isometric view of the hopper and a swirl chamber roof of the deagglomerator of the inhaler of FIG. 1;

FIG. 18 is a side elevation view of the deagglomerator of FIG. 17;

FIG. 19 is a top plan view of the deagglomerator of FIG. 17;

FIG. 20 is a bottom plan view of the deagglomerator of FIG. 17;

DETAILED DESCRIPTION OF CERTAIN EMBODIMENTS OF THE INVENTION

Figure 3:
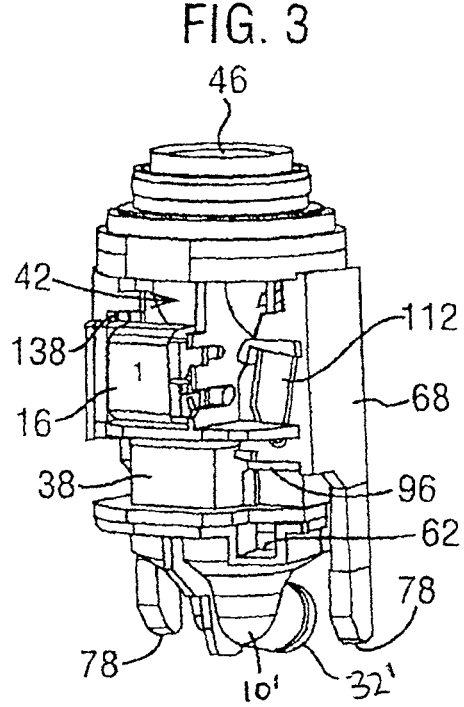
FIG. 3 is a second side isometric view of a main assembly of the inhaler of FIG. 1.

Several types of dry powder inhaler are known in the art. In a preferred embodiment of the present invention, the dry powder inhaler comprises the following features.

The preferred inhaler includes a delivery passageway for directing an inhalation-induced air flow through a mouthpiece, a channel extending from the delivery passageway to the medicament, and more preferably also a mouthpiece for patient inhalation, a delivery passageway for directing an inhalation-induced air flow through the mouthpiece, a channel extending from the delivery passageway, and a reservoir for containing medicament, with the reservoir having a dispenser port connected to the channel. In a preferred form, the dose metering system includes a cup received in the channel, which is movable between the dispenser port and the delivery passageway, a cup spring biasing the cup towards one of the dispenser port and the passageway, and a yoke movable between at least two positions. The yoke includes a ratchet engaging the cup and preventing movement of the cup when the yoke is in one of the positions, and allowing movement of the cup when the yoke is in another of the positions.

The inhaler preferably includes a cyclone deagglomerator for breaking up agglomerates of the active ingredients and carrier. This occurs prior to inhalation of the powder by a patient. The deagglomerator includes an inner wall defining a swirl chamber extending along an axis from a first end to a second end, a dry powder supply port, an inlet port, and an outlet port.

The supply port is in the first end of the swirl chamber for providing fluid communication between a dry powder delivery passageway of the inhaler and the first end of the swirl chamber. The inlet port is in the inner wall of the swirl chamber adjacent to the first end of the swirl chamber and provides fluid communication between a region exterior to the deagglomerator and the swirl chamber. The outlet port provides fluid communication between the second end of the swirl chamber and a region exterior to the deagglomerator.

A breath induced low pressure at the outlet port causes air flows into the swirl chamber through the dry powder supply port and the inlet port. The air flows collide with each other and with the wall of the swirl chamber prior to exiting through the outlet port, such that the active is detached from the carrier (lactose). The deagglomerator further includes vanes at the first end of the swirl chamber for creating additional collisions and impacts of entrained powder.

A first breath-actuated air flow is directed for entraining a dry powder from an inhaler into a first end of a chamber extending longitudinally between the first end and a second end, the first air flow directed in a longitudinal direction.

A second breath-actuated airflow is directed in a substantially transverse direction into the first end of the chamber such that the air flows collide and substantially combine.

Then, a portion of the combined air flows is deflected in a substantially longitudinal direction towards a second end of the chamber, and a remaining portion of the combined air flows is directed in a spiral path towards the second end of the chamber. All the combined air flows and any dry powder entrained therein are then delivered from the second end of the chamber to a patient's mouth.

The deagglomerator ensures that particles of the actives are small enough for adequate penetration of the powder into a bronchial region of a patient's lungs during inhalation by the patient.

Thus, in an embodiment of the present invention, the deagglomerator comprises: an inner wall defining a swirl chamber extending along an axis from a first end to a second end; a dry powder supply port in the first end of the swirl chamber for providing fluid communication between a dry powder delivery passageway of the inhaler and the first end of the swirl chamber; at least one inlet port in the inner wall of the swirl chamber adjacent to the first end of the swirl chamber providing fluid communication between a region exterior to the deagglomerator and the first end of the swirl chamber; an outlet port providing fluid communication between the second end of the swirl chamber and a region exterior to the deagglomerator; and vanes at the first end of the swirl chamber extending at least in part radially outwardly from the axis of the chamber, each of the vanes having an oblique surface facing at least in part in a direction transverse to the axis; whereby a breath induced low pressure at the outlet port causes air flows into the swirl chamber through the dry powder supply port and the inlet port.

The inhaler preferably has a reservoir for containing the medicament and an arrangement for delivering a metered dose of the medicament from the reservoir. The reservoir is typically a pressure system. The inhaler preferably includes: a sealed reservoir including a dispensing port; a channel communicating with the dispensing port and including a pressure relief port; a conduit providing fluid communication between an interior of the sealed reservoir and the pressure relief port of the channel; and a cup assembly movably received in the channel and including, a recess adapted to receive medicament when aligned with the dispensing port, a first sealing surface adapted to seal the dispensing port when the recess is unaligned with the dispensing port, and a second sealing surface adapted to sealing the pressure relief port when the recess is aligned with the dispensing port and unseal the pressure relief port when the recess is unaligned with the dispensing port.

The inhaler preferably has a dose counter. The inhaler includes a mouthpiece for patient inhalation, a dose-metering arrangement including a pawl movable along a predetermined path during the metering of a dose of medicament to the mouthpiece by the dose-metering arrangement, and a dose counter.

In a preferred form, the dose counter includes a bobbin, a rotatable spool, and a rolled ribbon received on the bobbin, rotatable about an axis of the bobbin. The ribbon has indicia thereon successively extending between a first end of the ribbon secured to the spool and a second end of the ribbon positioned on the bobbin. The dose counter also includes teeth extending radially outwardly from the spool into the predetermined path of the pawl so that the spool is rotated by the pawl and the ribbon advanced onto the spool during the metering of a dose to the mouthpiece.

The preferred inhaler includes a simple, accurate and consistent mechanical dose metering system that dispenses dry powdered medicament in discrete amounts or doses for patient inhalation, a reservoir pressure system that ensures consistently dispensed doses, and a dose counter indicating the number of doses remaining in the inhaler.

Figure 4:
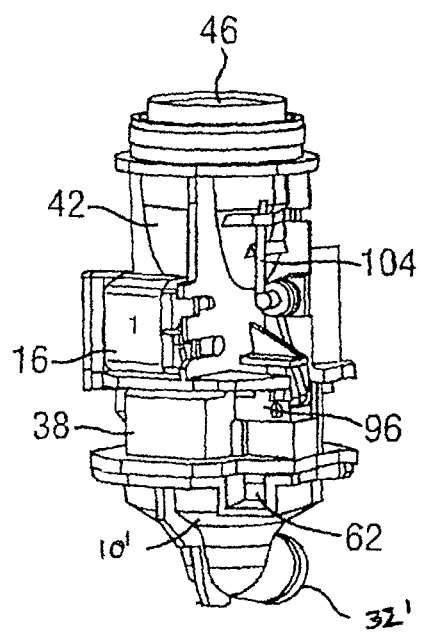
FIG. 4 is a second side isometric view of the main assembly of the inhaler of FIG. 1, shown with a yoke removed.
Figure 5:
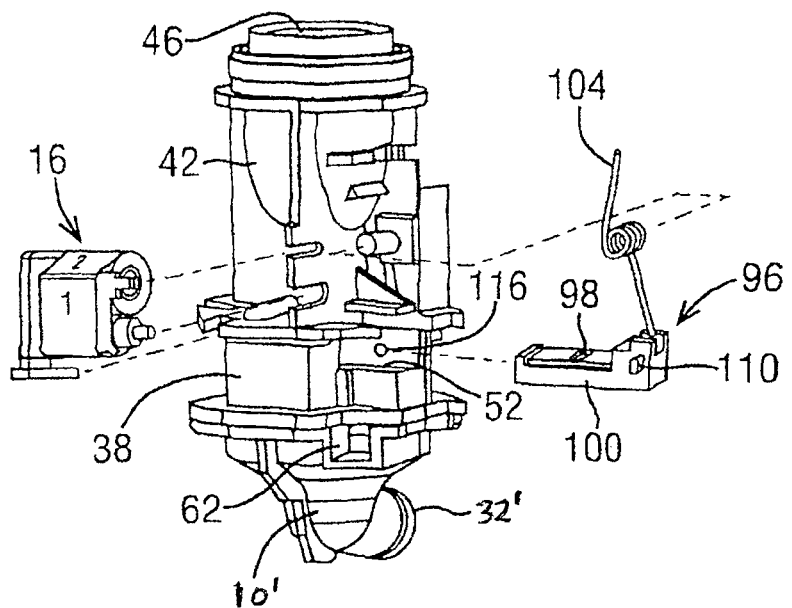
FIG. 5 is an exploded first side isometric view of the main assembly of the inhaler of FIG. 1.
Figure 6:
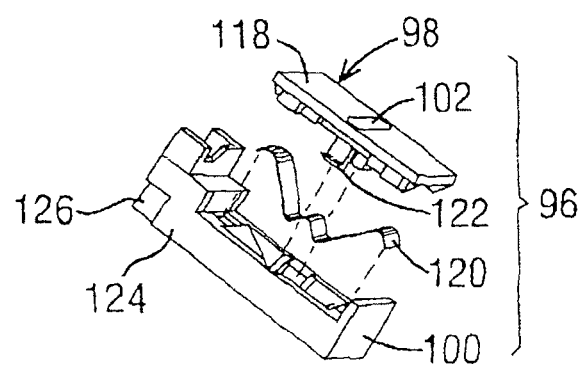
FIG. 6 is an exploded enlarged isometric view of a medicament cup of the inhaler of FIG. 1.
Figure 9:
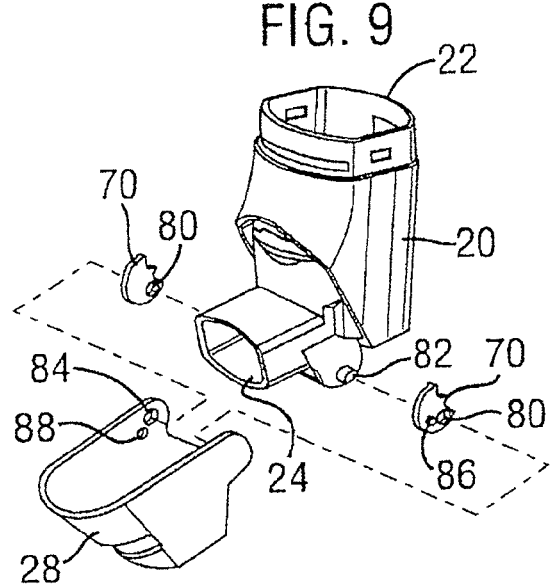
FIG. 9 is an exploded first side isometric view of a case, cams and a mouthpiece cover of the inhaler of FIG. 1.
Figure 10:
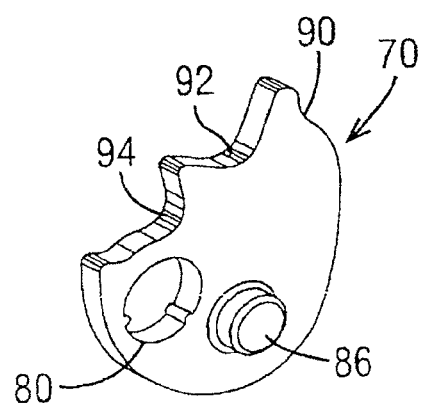
FIG. 10 is an enlarged side isometric view of one of the cams of the inhaler of FIG. 1.
Figure 11:
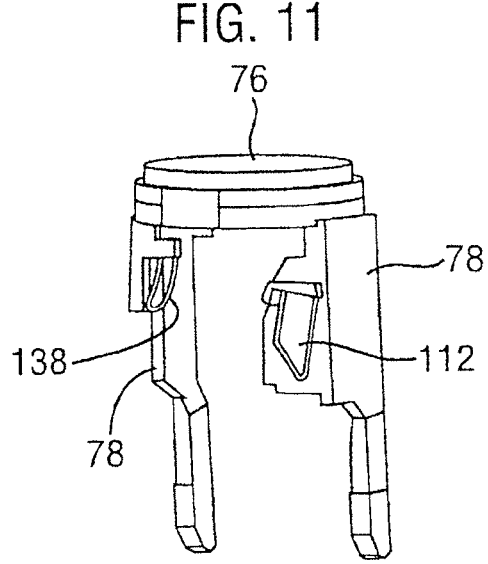
FIG. 11 is a second side isometric view of the yoke of the inhaler of FIG. 1.
Figure 12:
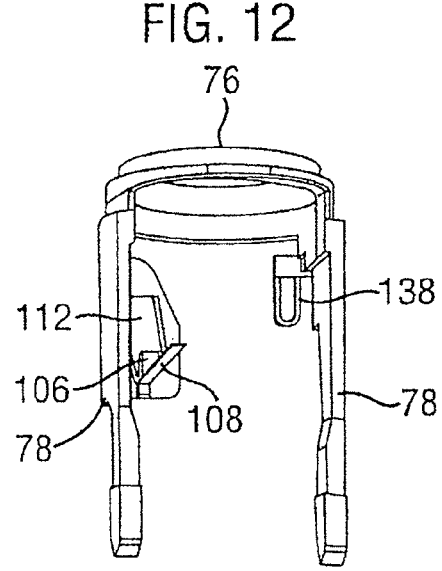
FIG. 12 is a first side isometric view of the yoke of the inhaler of FIG. 1, showing a ratchet and a push bar of the yoke.
Figure 13:
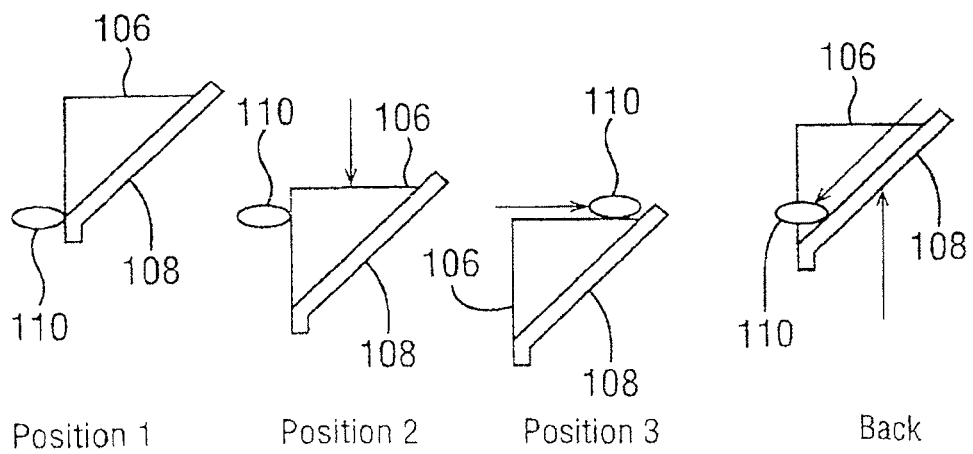
FIG. 13 is a schematic illustration of lateral movement of a boss of the medicament cup in response to longitudinal movement of the ratchet and the push bar of the yoke of the inhaler of FIG. 1.
Figure 14:
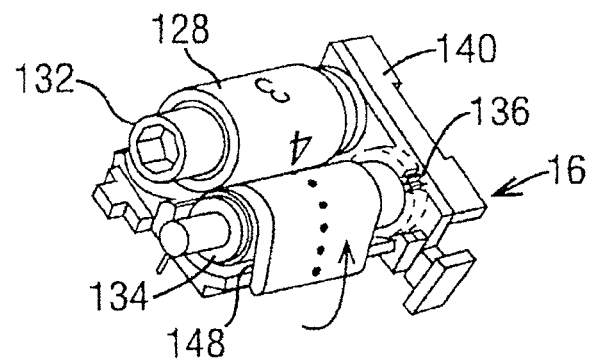
FIG. 14 is an enlarged isometric view of a dose counter of the inhaler of FIG. 1.
Figure 15:
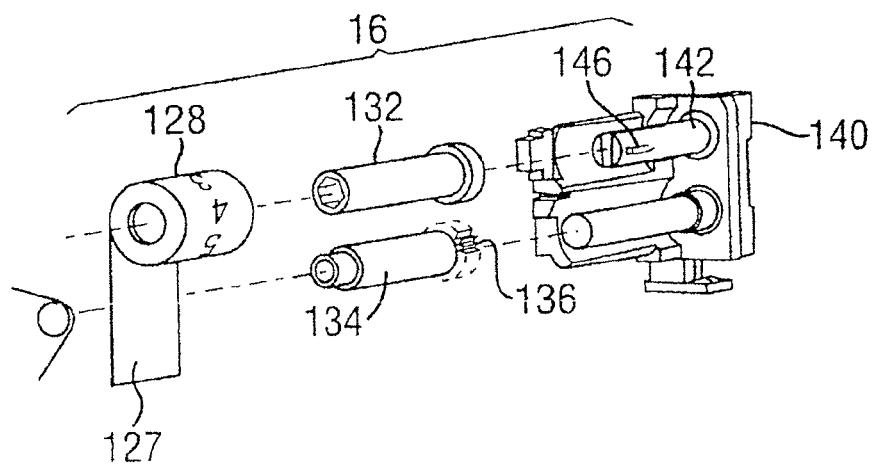
FIG. 15 is an exploded enlarged isometric view of the dose counter of the inhaler of FIG. 1.
Figure 16:
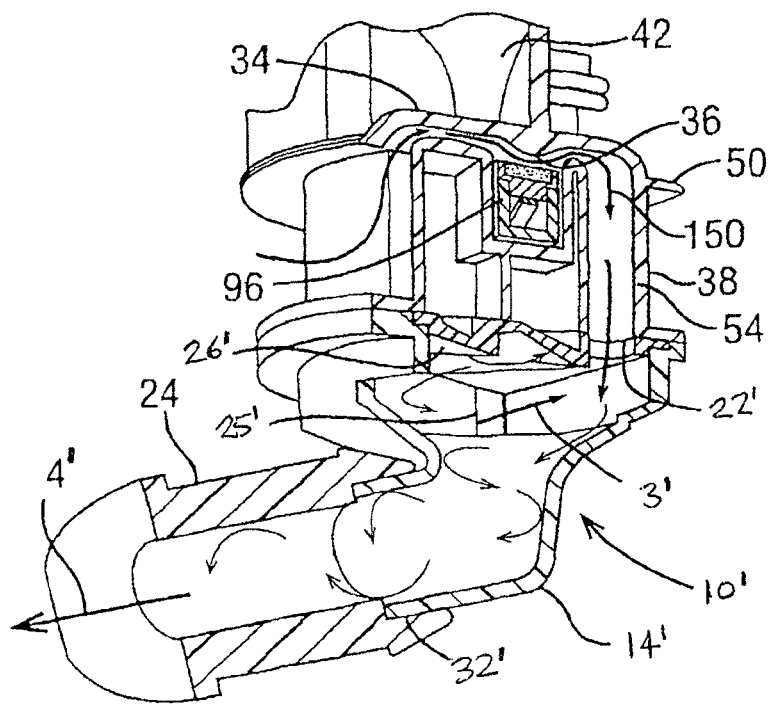
FIG. 16 is an enlarged isometric view, partially in section, of a portion of the inhaler of FIG. 1 illustrating medicament inhalation through the inhaler.

The present invention will now be described with reference to the drawings, in which:

FIG. 1 is a first side isometric view of a dry powder inhaler according to a preferred embodiment;

FIG. 2 is an exploded, second side isometric view of the inhaler of FIG. 1;

FIG. 3 is a second side isometric view of a main assembly of the inhaler of FIG. 1;

FIG. 4 is a second side isometric view of the main assembly of the inhaler of FIG. 1, shown with a yoke removed;

FIG. 5 is an exploded first side isometric view of the main assembly of the inhaler of FIG. 1;

FIG. 6 is an exploded enlarged isometric view of a medicament cup of the inhaler of FIG. 1;

FIG. 7 is an exploded first side isometric view of a hopper and a deagglomerator of the inhaler of FIG. 1;

FIG. 8 is an exploded second side isometric view of the hopper and a swirl chamber roof of the deagglomerator of the inhaler of FIG. 1;

FIG. 9 is an exploded first side isometric view of a case, cams and a mouthpiece cover of the inhaler of FIG. 1;

FIG. 10 is an enlarged side isometric view of one of the cams of the inhaler of FIG. 1;

FIG. 11 is a second side isometric view of the yoke of the inhaler of FIG. 1;

FIG. 12 is a first side isometric view of the yoke of the inhaler of FIG. 1, showing a ratchet and a push bar of the yoke;

FIG. 13 is a schematic illustration of lateral movement of a boss of the medicament cup in response to longitudinal movement of the ratchet and the push bar of the yoke of the inhaler of FIG. 1;

FIG. 14 is an enlarged isometric view of a dose counter of the inhaler of FIG. 1;

FIG. 15 is an exploded enlarged isometric view of the dose counter of the inhaler of FIG. 1; and FIG. 16 is an enlarged isometric view, partially in section, of a portion of the inhaler of FIG. 1 illustrating medicament inhalation through the inhaler.

Figure 17:
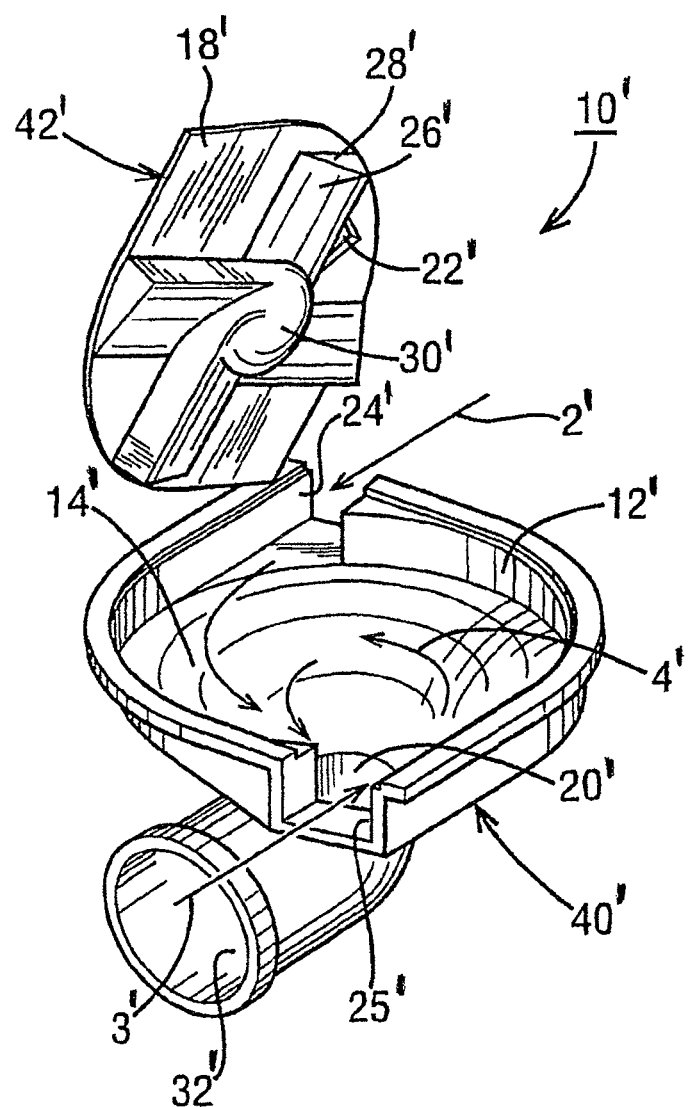
FIG. 17 is an exploded isometric view of a deagglomerator according to the present disclosure.
Figure 21:
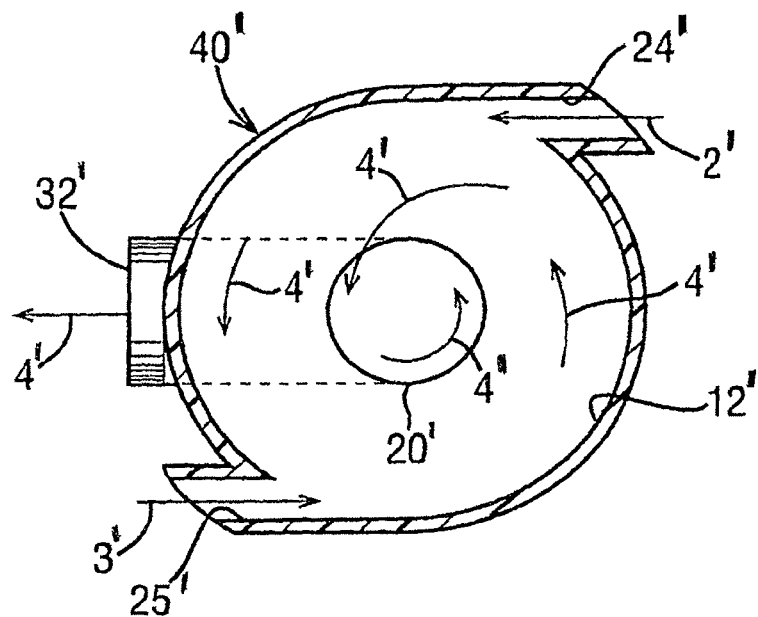
FIG. 21 is a sectional view of the deagglomerator of FIG. 17 taken along line 5'-5' of FIG. 18.
Figure 22:
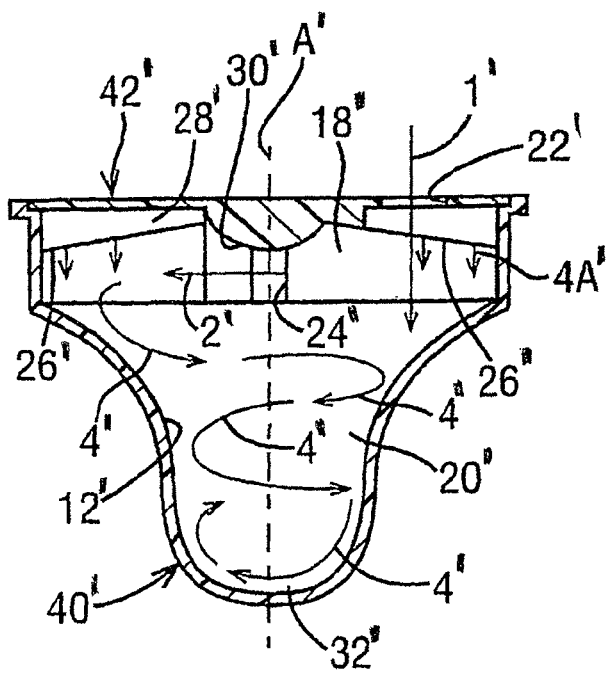
FIG. 22 is a sectional view of the deagglomerator of FIG. 17 taken along line 6'-6' of FIG. 19.

FIG. 17 is an exploded isometric view of a deagglomerator according to the present disclosure;

FIG. 18 is a side elevation view of the deagglomerator of FIG. 17;

FIG. 19 is a top plan view of the deagglomerator of FIG. 17;

FIG. 20 is a bottom plan view of the deagglomerator of FIG. 17;

FIG. 21 is a sectional view of the deagglomerator of FIG. 17 taken along line 5'-5' of FIG. 18; and FIG. 22 is a sectional view of the deagglomerator of FIG. 17 taken along line 6'-6' of FIG. 19.

The inhaler 10 generally includes a housing 18, and an assembly 12 received in the housing (see FIG. 2). The housing 18 includes a case 20 having an open end 22 and a mouthpiece 24 for patient inhalation, a cap 26 secured to and closing the open end 22 of the case 20, and a cover 28 pivotally mounted to the case 20 for covering the mouthpiece 24 (see FIGS. 1, 2 and 9). The housing 18 is preferably manufactured from a plastic such as polypropylene, acetal or moulded polystyrene, but may be manufactured from metal or another suitable material.

The internal assembly 12 includes a reservoir 14 for containing dry powered medicament in bulk form, a deagglomerator 10' that breaks down the medicament between a delivery passageway 34 and the mouthpiece 24, and a spacer 38 connecting the reservoir to the deagglomerator.

The reservoir 14 is generally made up of a collapsible bellows 40 and a hopper 42 having an dispenser port 44 (see FIGS. 2-5 and 7-8) for dispensing medicament upon the bellows 40 being at least partially collapsed to reduce the internal volume of the reservoir.

The hopper 42 is for holding the dry powder medicament in bulk form and has an open end 46 closed by the flexible accordion-like bellows 40 in a substantially air-tight manner.

An air filter 48 covers the open end 46 of the hopper 42 and prevents dry powder medicament from leaking from the hopper 42 (see FIG. 7).

A base 50 of the hopper 42 is secured to a spacer 38, which is in turn secured to the deagglomerator 10' (see FIGS. 3-5 and 7-8). The hopper 42, the spacer 38, and the deagglomerator 10' are preferably manufactured from a plastic such as polypropylene, acetal or moulded polystyrene, but may be manufactured from metal or another suitable material.

The hopper 42, the spacer 38 and the deagglomerator 10' are connected in a manner that provides an air tight seal between the parts. For this purpose heat or cold sealing, laser welding or ultrasonic welding could be used, for example.

The spacer 38 and the hopper 42 together define the medicament delivery passageway 34, which preferably includes a venturi 36 (see FIG. 16) for creating an entraining air flow. The spacer 38 defines a slide channel 52 communicating with the dispenser port 44 of the hopper 42, and a chimney 54 providing fluid communication between the medicament delivery passageway 34 and a supply port 22' of the deagglomerator 10' (see FIGS. 7 and 8). The slide channel 52 extends generally normal with respect to the axis "A" of the inhaler 10.

The deagglomerator 10' breaks down agglomerates of dry powder medicament before the dry powder leaves the inhaler 10 through the mouthpiece 24.

Referring to FIGS. 17 to 22, the deagglomerator 10' breaks down agglomerates of medicament, or medicament and carrier, before inhalation of the medicament by a patient.

In general, the deagglomerator 10' includes an inner wall 12' defining a swirl chamber 14' extending along an axis A' from a first end 18' to a second end 20'. The swirl chamber 14' includes circular cross-sectional areas arranged transverse to the axis A', that decrease from the first end 18' to the second end 20' of the swirl chamber 14', such that any air flow traveling from the first end of the swirl chamber to the second end will be constricted and at least in part collide with the inner wall 12' of the chamber.

Preferably, the cross-sectional areas of the swirl chamber 14' decrease monotonically. In addition, the inner wall 12' is preferably convex, i.e., arches inwardly towards the axis A', as shown best in FIG. 22.

As shown in FIGS. 17, 19 and 22, the deagglomerator 10' also includes a dry powder supply port 22' in the first end 18' of the swirl chamber 14' for providing fluid communication between a dry powder delivery passageway of an inhaler and the first end 18' of the swirl chamber 14'. Preferably, the dry powder supply port 22' faces in a direction substantially parallel with the axis A' such that an air flow, illustrated by arrow 1' in FIG. 22, entering the chamber 14' through the supply port 22' is at least initially directed parallel with respect to the axis A' of the chamber.

Referring to FIGS. 17 to 22, the deagglomerator 10' additionally includes at least one inlet port 24' in the inner wall 12' of the swirl chamber 14' adjacent to or near the first end 18' of the chamber providing fluid communication between a region exterior to the deagglomerator and the first end 18' of the swirl chamber 14'. Preferably, the at least one inlet port comprises two diametrically opposed inlet ports 24', 25' that extend in a direction substantially transverse to the axis A' and substantially tangential to the circular cross-section of the swirl chamber 14'. As a result, air flows, illustrated by arrows 2' and 3' in FIGS. 17 and 21, entering the chamber 14' through the inlet ports are at least initially directed transverse with respect to the axis A' of the chamber and collide with the air flow 1' entering through the supply port 22' to create turbulence. The combined air flows, illustrated by arrow 4' in FIGS. 21 and 22, then collide with the inner wall 12' of the chamber 14', form a vortex, and create additional turbulence as they move towards the second end 20' of the chamber.

Referring to FIGS. 17-19 and 22, the deagglomerator 10' includes vanes 26' at the first end 18' of the swirl chamber 14' extending at least in part radially outwardly from the axis A' of the chamber. Each of the vanes 26' has an oblique surface 28' facing at least in part in a direction transverse to the axis A' of the chamber. The vanes 26' are sized such that at least a portion 4A' of the combined air flows 4' collide with the oblique surfaces 28', as shown in FIG. 22. Preferably, the vanes comprise four vanes 26', each extending between a hub 30' aligned with the axis A' and the wall 12' of the swirl chamber 14'.

As shown in FIGS. 17 to 22, the deagglomerator 10' further includes an outlet port 32' providing fluid communication between the second end 20' of the swirl chamber 14' and a region exterior to the deagglomerator. A breath induced low pressure at the outlet port 32' causes the air flow 1' through the supply port 22' and the air flows 2',3' through the inlet ports and draws the combined air flow 4' through the swirl chamber 14'. The combined air flow 4' then exits the deagglomerator through the outlet port 32'. Preferably the outlet port 32' extends substantially transverse to the axis A', such that the air flow 4' will collide with an inner wall of the outlet port 32' and create further turbulence.

During use of the deagglomerator 10' in combination with the inhaler, patient inhalation at the outlet port 32' causes air flows 1',2',3' to enter through, respectively, the dry powder supply port 22' and the inlet ports. Although not shown, the air flow 1' through the supply port 22' entrains the dry powder into the swirl chamber 14'. The air flow 1' and entrained dry powder are directed by the supply port 22' into the chamber in a longitudinal direction, while the air flows 2',3' from the inlet ports are directed in a transverse direction, such that the air flows collide and substantial combine.

A portion of the combined air flow 4' and the entrained dry powder then collide with the oblique surfaces 28' of the vanes 26' causing particles and any agglomerates of the dry powder to impact against the oblique surfaces and collide with each other. The geometry of the swirl chamber 14' causes the combined air flow 4' and the entrained dry powder to follow a turbulent, spiral path, or vortex, through the chamber. As will be appreciated, the decreasing cross-sections of the swirl chamber 14' continuously changes the direction and increases the velocity of the spiralling combined air flow 4' and entrained dry powder. Thus, particles and any agglomerates of the dry powder constantly impact against the wall 12' of the swirl chamber 14' and collide with each other, resulting in a mutual grinding or shattering action between the particles and agglomerates. In addition, particles and agglomerates deflected off the oblique surfaces 28' of the vanes 26' cause further impacts and collisions.

Upon exiting the swirl chamber 14', the direction of the combined air flow 4 and the entrained dry powder is again changed to a transverse direction with respect to the axis A', through the outlet port 32'. The combined air flow 4' and the entrained dry powder retain a swirl component of the flow, such that the air flow 4' and the entrained dry powder spirally swirls through the outlet port 32'. The swirling flow causes additional impacts in the outlet port 32' so as to result in further breaking up of any remaining agglomerates prior to being inhaled by a patient.

As shown in FIGS. 17 to 22, the deagglomerator is preferably assembly from two pieces: a cup-like base 40' and a cover 42'. The base 40' and the cover 42' are connected to form the swirl chamber 14'. The cup-like base 40' includes the wall 12' and the second end 20' of the chamber and defines the outlet port 32'. The base 40' also includes the inlet ports of the swirl chamber 14'. The cover 42' forms the vanes 26' and defines the supply port 22'.

The base 40' and the cover 42' of the deagglomerator are preferably manufactured from a plastic such as polypropylene, acetal or moulded polystyrene, but may be manufactured from metal or another suitable material. Preferably, the cover 42' includes an anti-static additive, so that dry powder will not cling to the vanes 26'. The base 40' and the cover 42' are then connected in a manner that provides an air tight seal between the parts. For this purpose heat or cold sealing, laser welding or ultra-sonic welding could be used, for example.

Although the inhaler 10 is shown with a particular deagglomerator 10', the inhaler 10 is not limited to use with the deagglomerator shown and can be used with other types of deagglomerators or a simple swirl chamber.

The dose metering system includes a first yoke 66 and a second yoke 68 mounted on the internal assembly 12 within the housing 18, and movable in a linear direction parallel with an axis "A" of the inhaler 10 (see FIG. 2). An actuation spring 69 is positioned between the cap 26 of the housing 18 and the first yoke 66 for biasing the yokes in a first direction towards the mouthpiece 24. In particular, the actuation spring 69 biases the first yoke 66 against the bellows 40 and the second yoke 68 against cams 70 mounted on the mouthpiece cover 28 (see FIG. 9).

The first yoke 66 includes an opening 72 that receives and retains a crown 74 of the bellows 40 such that the first yoke 66 pulls and expands the bellows 40 when moved towards the cap 26, i.e., against the actuation spring 69 (see FIG. 2). The second yoke 68 includes a belt 76, which receives the first yoke 66, and two cam followers 78 extending from the belt in a direction opposite the first yoke 66 (see FIGS. 3, 11 and 12), towards the cams 70 of the mouthpiece cover 28 (FIGS. 9,10).

The dose metering system also includes the two cams 70 mounted on the mouthpiece cover 28 (see FIGS. 9 and 10), and movable with the cover 28 between open and closed positions. The cams 70 each include an opening 80 for allowing outwardly extending hinges 82 of the case 20 to pass therethrough and be received in first recesses 84 of the cover 28. The cams 70 also include bosses 86 extending outwardly and received in second recesses 88 of the cover 28, such that the cover 28 pivots about the hinges 82 and the cams 70 move with the cover 28 about the hinges.

Each cam 70 also includes first, second and third cam surfaces 90,92,94, and the cam followers 78 of the second yoke 68 are biased against the cam surfaces by the actuation spring 69. The cam surfaces 90,92,94 are arranged such the cam followers 78 successively engage the first cam surfaces 90 when the cover 28 is closed, the second cam surfaces 92 when the cover 28 is partially opened, and the third cam surfaces 94 when the cover 28 is fully opened. The first cam surfaces 90 are spaced further from the hinges 82 than the second and the third cam surfaces, while the second cam surfaces 92 are spaced further from the hinges 82 than the third cam surfaces 94. The cams 70, therefore, allow the yokes 66,68 to be moved by the actuation spring 69 parallel with the axis "A" of the inhaler 10 in the first direction (towards the mouthpiece 24) through first, second and third positions as the cover 28 is opened. The cams 70 also push the yokes 66, 68 in a second direction parallel with the axis "A" (against the actuation spring 69 and towards the cap 26 of the housing 18) through the third, the second and the first positions as the cover 28 is closed.

The dose metering system further includes a cup assembly 96 movable between the dispenser port 44 of the reservoir 14 and the delivery passageway 34. The cup assembly 96 includes a medicament cup 98 mounted in a sled 100 slidably received in the slide channel 52 of the spacer 38 below the hopper 42 (see FIGS. 5 and 6). The medicament cup 98 includes a recess 102 adapted to receive medicament from the dispenser port 44 of the reservoir 14 and sized to hold a predetermined dose of dry powdered medicament when filled. The cup sled 100 is biased along the slide channel 52 from the dispenser port 44 of the hopper 42 towards the delivery passageway 34 by a cup spring 104, which is secured on the hopper 42 (see FIGS. 4 and 5).

The dose metering system also includes a ratchet 106 and a push bar 108 on one of the cam followers 78 of the second yoke 68 that engage a boss 110 of the cup sled 100 (see FIGS. 5,11 and 12). The ratchet 106 is mounted on a flexible flap 112 and is shaped to allow the boss 110 of the sled 100 to depress and pass over the ratchet 106, when the boss 110 is engaged by the push bar 108. Operation of the dose metering system is discussed below.

The reservoir pressure system includes a pressure relief conduit 114 in fluid communication with the interior of the reservoir 14 (see FIGS. 7 and 8), and a pressure relief port 116 in a wall of the slide channel 52 (see FIGS. 5 and 8) providing fluid communication with the pressure relief conduit 114 of the hopper 42.

The medicament cup assembly 96 includes a first sealing surface 118 adapted to seal the dispenser port 44 upon the cup assembly being moved to the delivery passageway 34 (see FIGS. 5 and 6). A sealing spring 120 is provided between the sled 100 and the cup 98 for biasing the medicament cup 98 against a bottom surface of the hopper 42 to seal the dispenser port 44 of the reservoir 14. The cup 98 includes clips 122 that allow the cup to be biased against the reservoir, yet retain the cup in the sled 100.

The sled 100 includes a second sealing surface 124 adapted to seal the pressure relief port 116 when the recess 102 of the cup 98 is aligned with the dispenser port 44, and an indentation 126 (see FIG. 6) adapted to unseal the pressure relief port 116 when the first sealing surface 118 is aligned with the dispenser port 44. Operation of the pressure system is discussed below.

The dose counting system 16 is mounted to the hopper 42 and includes a ribbon 128, having successive numbers or other suitable indicia printed thereon, in alignment with a transparent window 130 provided in the housing 18 (see FIG. 2). The dose counting system 16 includes a rotatable bobbin 132, an indexing spool 134 rotatable in a single direction, and the ribbon 128 rolled and received on the bobbin 132 and having a first end 127 secured to the spool 134, wherein the ribbon 128 unrolls from the bobbin 132 so that the indicia is successively displayed as the spool 134 is rotated or advanced.

The spool 134 is arranged to rotate upon movement of the yokes 66,68 to effect delivery of a dose of medicament from the reservoir 14 into the delivery passageway 34, such that the number on the ribbon 128 is advanced to indicate that another dose has been dispensed by the inhaler 10. The ribbon 128 can be arranged such that the numbers, or other suitable indicia, increase or decrease upon rotation of the spool 134. For example, the ribbon 128 can be arranged such that the numbers, or other suitable indicia, decrease upon rotation of the spool 134 to indicate the number of doses remaining in the inhaler 10.

Alternatively, the ribbon 128 can be arranged such that the numbers, or other suitable indicia, increase upon rotation of the spool 134 to indicate the number of doses dispensed by the inhaler 10.

The indexing spool 134 preferably includes radially extending teeth 136, which are engaged by a pawl 138 extending from one of the cam followers 78 (see FIGS. 3 and 11) of the second yoke 68 upon movement of the yoke to rotate, or advance, the indexing spool 134. More particularly, the pawl 138 is shaped and arranged such that it engages the teeth 136 and advances the indexing spool 134 only upon the mouthpiece 24 cover 28 being closed and the yokes 66,68 moved back towards the cap 26 of the housing 18.

The dose counting system 16 also includes a chassis 140 that secures the dose counting system to the hopper 42 and includes shafts 142,144 for receiving the bobbin 132 and the indexing spool 134. The bobbin shaft 142 is preferably forked and includes radially nubs 146 for creating a resilient resistance to rotation of the bobbin 132 on the shaft 142. A clutch spring 148 is received on the end of the indexing spool 134 and locked to the chassis 140 to allow rotation of the spool 134 in only a single direction (anticlockwise as shown in FIG. 14). Operation of the dose counting system 16 is discussed below.

FIG. 13 illustrates the relative movements of the boss 110 of the cup sled 100, and the ratchet 106 and the push bar 108 of the second yoke 68 as the mouthpiece cover 28 is opened and closed. In the first position of the yokes 66,68 (wherein the cover 28 is closed and the cam followers 78 are in contact with the first cam surfaces 90 of the cams 70), the ratchet 106 prevents the cup spring 104 from moving the cup sled 100 to the delivery passageway 34. The dose metering system is arranged such that when the yokes are in the first position, the recess 102 of the medicament cup 98 is directly aligned with the dispenser port 44 of the reservoir 14 and the pressure relief port 116 of the spacer 38 is sealed by the second sealing surface 124 of the cup sled 100.

Upon the cover 28 being partially opened such that the second cam surfaces 92 of the cams 70 engage the cam followers 78, the actuator spring 69 is allowed to move the yokes 66,68 linearly towards the mouthpiece 24 to the second position and partially collapse the bellows 40 of the medicament reservoir 14. The partially collapsed bellows 40 pressurizes the interior of the reservoir 14 and ensures medicament dispensed from the dispenser port 44 of the reservoir 14 fills the recess 102 of the medicament cup 98 such that a predetermined dose is provided. In the second position, however, the ratchet 106 prevents the cup sled 100 from being moved to the delivery passageway 34, such that the recess 102 of the medicament cup 98 remains aligned with the dispenser port 44 of the reservoir 14 and the pressure relief port 116 of the spacer 38 remains sealed by the second sealing surface 124 of the cup assembly 96.

Upon the cover 28 being fully opened such that the third cam surfaces 94 engage the cam followers 78, the actuator spring 69 is allowed to move the yokes 66,68 further towards the mouthpiece 24 to the third position. When moved to the third position, the ratchet 106 disengages, or falls below the boss 110 of the cup sled 100 and allows the cup sled 100 to be moved by the cup spring 104, such that the filled recess 102 of the cup 98 is position in the venturi 36 of the delivery passageway 34 and the dispenser port 44 of the reservoir 14 is sealed by the first sealing surface 118 of the cup assembly 96. In addition, the pressure relief port 116 is uncovered by the indentation 126 in the side surface of the sled 100 to release pressure from the reservoir 14 and allow the bellows 40 to further collapse and accommodate the movement of the yokes 66,68 to the third position. The inhaler 10 is then ready for inhalation by a patient of the dose of medicament placed in the delivery passageway 34.

As shown in FIG. 16, a breath-induced air stream 4' diverted through the delivery passageway 34 passes through the venturi 36, entrains the medicament and carries the medicament into the deagglomerator 10' of the inhaler 10. Two other breath-induced air streams 2', 3' (only one shown) enter the deagglomerator 10' through the diametrically opposed inlet ports 24', 25' and combine with the medicament entrained air stream 150 from the delivery passageway 34. The combined flows 4' and entrained dry powder medicament then travel to the outlet port 32' of the deagglomerator and pass through the mouthpiece 24 for patient inhalation.

Once inhalation is completed, the mouthpiece cover 28 can be closed. When the cover 28 is closed, the trigger cams 70 force the yokes 66,68 upwardly such that the first yoke 66 expands the bellows 40, and the pawl 138 of the second yoke 68 advances the indexing spool 134 of the dose counting system 16 to provide a visual indication of a dose having been dispensed. In addition, the cup assembly 96 is forced back to the first position by the pusher bar 108 of the upwardly moving second yoke 68 (see FIG. 13) such that the boss 110 of the cup sled 100 is engaged and retained by the ratchet 106 of the second yoke 68.

The medicament used in the inhaler of the present invention comprises a mixture of micronised fluticasone propionate, micronised salmeterol xinafoate and a lactose carrier. Micronising may be performed by any suitable technique known in the art, e.g. jet milling.

The medicament contains fluticasone propionate. It is preferable that substantially all of the particles of fluticasone propionate are less than 10 µm in size. This is to ensure that the particles are effectively entrained in the air stream and deposited in the lower lung, which is the site of action. Preferably, the particle size distribution of the fluticasone propionate is: d10=0.4-1.1 µm, d50=1.1-3.0 µm, d90=2.6-7.5 µm and NLT95%<10 µm; more preferably d10=0.5-1.0 µm, d50=1.8-2.6 µm, d90=3.0-6.5 µm and NLT99%<10 µm; and most preferably d10=0.5-1.0 µm, d50=1.90-2.50 µm, d90=3.5-6.5 µm and NLT99%<10 µm.

The particle size of the fluticasone propionate may be measured by laser diffraction as an aqueous dispersion, e.g. using a Malvern Mastersizer 2000 instrument. In particular, the technique is wet dispersion. The equipment is set with the following optical parameters: Refractive index for fluticasone propionate=1.530, Refractive index for dispersant water=1.330, Absorption=3.0 and Obscuration=10-30%. The sample suspension is prepared by mixing approximately 50 mg sample with 10 ml of de-ionized water containing 1% Tween® 80 in a 25 ml glass vessel. The suspension is stirred with a magnetic stirrer for 2 mins at moderate speed. The Hydro 2000S dispersion unit tank is filled with about 150 ml de-ionized water. The de-ionized water is sonicated by setting the ultrasonics at the level of 100% for 30 seconds and then the ultrasonic is turned back down to 0%. The pump/stirrer in the dispersion unit tank is turned to 3500 rpm and then down to zero to clear any bubbles. About 0.3 ml of 1% TA-10X FG defoamer is added into the dispersion media and the pump/stirrer is turned to 2000 rpm and then the background is measured. Slowly the prepared suspension samples are dropped into the dispersion unit until a stabilized initial obscuration at 10-20% is reached. The sample is continued to be stirred in the dispersion unit for about 1 min at 2000 rpm, then the ultrasound is turned on and the level is set to 100%. After sonicating for 5 min with both the pump and ultrasound on, the sample is measured three times. The procedure is repeated two more times.

The delivered dose of fluticasone propionate is less than 100 µg per actuation, more preferably less than 90 µg per actuation, more preferably less than 75 µg per actuation, and most preferably less than 60 µg per actuation.

The medicament contains salmeterol xinafoate. It is preferable that substantially all of the particles of salmeterol xinafoate are less than 10 µm in size. This is to ensure that the particles are effectively entrained in the air stream and deposited in the lower lung, which is the site of action. Preferably, the particle size distribution of the salmeterol xinafoate is: d10=0.4-1.3 µm, d50=1.4-3.0 µm, d90=2.4-6.5 µm and NLT95%<10 µm; more preferably d10=0.6-1.1 µm, d50=1.75-2.65 µm, d90=2.7-5.5 µm and NLT99%<10 µm; most preferably d10=0.7-1.0 µm, d50=2.0-2.4 µm, d90=3.9-5.0 µm and NLT99%<10 µm.

The particle size of the salmeterol xinafoate may be measured using the same methodology as described for fluticasone propionate. In particular, the technique is wet dispersion. The equipment is set with the following optical parameters: Refractive index for salmeterol xinafoate=1.500, Refractive index for dispersant water=1.330, Absorption=0.1 and Obscuration=10-30%. The sample suspension is prepared by mixing approximately 50 mg sample with 10 ml of de-ionized water containing 1% Tween® 80 in a 25 ml glass vessel. The suspension is stirred with a magnetic stirrer for 2 mins at moderate speed. The Hydro 2000S dispersion unit tank is filled with about 150 ml de-ionized water. The de-ionized water is sonicated by setting the ultrasonics at the level of 100% for 30 seconds and then the ultrasonic is turned back down to 0%. The pump/stirrer in the dispersion unit tank is turned to 3500 rpm and then down to zero to clear any bubbles. About 0.3 ml of 1% TA-10X FG defoamer is added into the dispersion media and the pump/stirrer is turned to 2250 rpm and then the background is measured. The prepared suspension samples are slowly dropped into the dispersion unit until a stabilized initial obscuration at 15-20% is reached. The sample is continued to be stirred in the dispersion unit for about 1 min at 2250 rpm, then the ultrasound is turned on and the level is set to 100%. After sonicating for 3 min with both the pump and ultrasound on, the sample is measured three times. The procedure is repeated two more times.

The delivered dose of salmeterol xinafoate (as base) is preferably 1-100 μg per actuation, more preferably 5-50 μg per actuation, based on the amount salmeterol present (i.e. the amount is calculated without including contribution to the mass of the counterion).

Particularly preferred delivered doses of fluticasone propionate/salmeterol xinafoate in μg are 50/12.5 or 25/12.5.

The inhaler of the present invention administers a delivered dose of fluticasone propionate/salmeterol xinafoate which provides a baseline-adjusted $FEV_1$ in a patient of more than 150 mL within 30 minutes of receiving the dose. The baseline-adjusted $FEV_1$ preferably remains above 150 mL for at least 6 hours after receiving the dose.

The delivered dose of the active agent is measured as per the USP<601>, using the following method. A vacuum pump (MSP HCP-5) is connected to a regulator (Copley TPK 2000), which is used for adjusting the required drop pressure $P_1$ in a DUSA sampling tube (Dosage Unit Sampling Apparatus, Copley). The inhaler is inserted into a mouthpiece adaptor, ensuring an airtight seal. $P_1$ is adjusted to a pressure drop of 4.0 KPa (3.95-4.04 KPa) for the purposes of sample testing. After actuation of the inhaler, the DUSA is removed and the filter paper pushed inside with the help of a transfer pipette. Using a known amount of solvent (acetonitrile:methanol: water (40:40:20)), the mouthpiece adaptor is rinsed into the DUSA. The DUSA is shaken to dissolve fully the sample. A portion of the sample solution is transferred into a 5 mL syringe fitted with Acrodisc PSF 0.45 μm filter. The first few drops from the filter are discarded and the filtered solution is transferred into a UPLC vial. A standard UPLC technique is then used to determine the amount of active agent delivered into the DUSA. The delivered doses of the inhaler are collected at the beginning, middle and end of inhaler life on three different days.

It is preferable that substantially all of the particles of lactose are less than 300 μm in size. It is preferable that the lactose carrier includes a portion of fine material, that is, lactose particles of less than 10 μm in size. The fine lactose fraction may be present in an amount of 1-10 wt %, more preferably 2.5-7.5 wt %, based on the total amount of lactose. Preferably, the particle size distribution of the lactose fraction is dl 0=15-50 μm, d50=80-120 μm, d90=120-200 μm, NLT99%<300 μm and 1.5-8.5%<10 μm. Most preferably, the particle size distribution of the lactose fraction is d10=25-40 μm, d50=87-107 μm, d90=140-180 μm, NLT99%<300 μm and 2.5-7.5%<10 μm. The lactose is preferably α-lactose monohydrate (e.g. from DMV Fronterra Excipients).

The particle size distribution of the lactose provided herein is measured by laser diffraction in air, e.g. with a Sympatec HELOS/BF equipped with a RODOS disperser and VIBRI feeder unit. In particular, lens type R5: 05/4.5 . . . 875 μm is used; The following information is set on the equipment: density=1.5500 $g/cm^3$, shape factor=1.00, calculation mode=HRLD, forced stability=0; The following trigger conditions are set: Name=CH12, 0.2%, reference duration=10s (single), time base=100 ms, focus prior to first measurement=Yes, normal measurement=standard mode, start=0.000 s, channel 12≥0.2%, valid=always, stop after=5.000 s, channel 12≤0.2%, or after=60.000 s, real time, repeat measurement=0, repeat focus=No; The following disperser conditions are set: Name 1.5 bar; 85%; 2.5 mm, dispersing type=RODOS/M, injector=4 mm, with=0 cascade elements, primary pressure=1.5 bar, always auto adjust before ref. meas.=No, feeder type=VIBRI, feed rate=85%, gap width=2.5 mm, funnel rotation=0%, cleaning time=10 s, use VIBRI Control=No, vacuum extraction type=Nilfisk, delay=5 s. An adequate amount of approximate 5 g of the sample is transferred into a weighing paper using a clean dry stainless steel spatula, and then poured into the funnel on the VIBRI chute. The sample is measured. The pressure is maintained at about 1.4-1.6 bar, measurement time=1.0-10.0 seconds, $C_{opt}$=5-15% and vacuum≤7 mbar. The procedure is repeated two more times.

The inhaler described herein is provided for the treatment of asthma or COPD.

EXAMPLES

Example 1

Dry powder formulations were prepared using the following ingredients:

- fluticasone propionate having a particle size of d10=0.5-0.9 μm, d50=1.5-2.4 μm, d90=3.3-6.0 μm, and NLT99%<10 μm.
- salmeterol xinafoate having a particle size of d10=0.6-1.1 μm, d50=1.75-2.65 μm, d90=2.7-5.5 μm, and NLT99%<10 μm.
- α-lactose monohydrate (DMV Fronterra Excipients) having a particle size of d10=25-40 μm, d50=87-107 μm, d90=140-180 μm, NLT99%<300 μm and 3-9%<10 μm, Formulations were provided having delivered doses of fluticasone propionate/salmeterol xinafoate of 12.5/50, 25/50, 50/50 and 100/50 mcg. (The first three are of the invention, the fourth is a reference example.)

Further formulations were provided having delivered doses of fluticasone propionate/salmeterol of 49/12.75 and 100/12.75 mcg. (Salmeterol is delivered as 18.52 mcg of salmeterol xinafoate.)

Example 2

A six-period crossover, dose-ranging study is performed to evaluate the efficacy and safety of multiple doses of FS Spiromax® (fluticasone propionate/salmeterol xinafoate inhalation powder) administered as single doses compared with Advair Diskus in adult and adolescent subjects with persistent asthma.

Fluticasone propionate/salmeterol xinafoate Spiromax is manufactured by Teva Pharmaceuticals. The specifications are as set out in Example 1. Doses tested contain fluticasone propionate 12.5, 25, 49, 50 and 100 mcg. Advair Diskus is manufactured by GlaxoSmithKline and is a commercially available product. The label claim dose of fluticasone propionate/salmeterol xinafoate of Advair Diskus is 100/50 mcg.

Assessments were performed using forced expiratory volume in 1 second ($FEV_1$) measurements. The study included a run-in period is to complete baseline safety evaluations and to obtain baseline measures of asthma status, including baseline $FEV_1$ measurements.

It is found that the product of the present invention provided comparable efficacy (as determined by $FEV_1$ measurements) despite having a lower dose of fluticasone propionate. Lower plasma concentrations are also observed for delivered doses of fluticasone propionate of 12.5, 25, 49 and 50 mcg.

Example 3

A study is performed to evaluate the efficacy and safety of multiple doses of FS Spiromax® (fluticasone propionate/salmeterol xinafoate multidose dry powder inhaler or FS MDPI) when administered over 12 weeks in patients 12 years of age and older with persistent asthma.

FS MDPI is manufactured by Teva Pharmaceuticals. FS MDPI Formulations tested delivered doses of fluticasone propionate/salmeterol of 49/12.75 and 100/12.75 mcg. (Salmeterol is delivered as 18.52 mcg of salmeterol xinafoate.) A placebo containing no active pharmaceutical ingredient was also provided in this study.

Assessments were performed using forced expiratory volume in 1 second ($FEV_1$) measurements. The study included a run-in period is to complete baseline safety evaluations and to obtain baseline measures of asthma status, including baseline $FEV_1$ measurements.

It was also found that the FS MDPI provided significantly greater benefits at each dose versus placebo. The safety profile of FS MDPI was comparable to placebo.

What is claimed is:

1. A dry powder inhaler comprising:
   a dry powder medicament comprising fluticasone propionate, salmeterol xinafoate and a lactose carrier;
   wherein, the delivered dose of fluticasone propionate per actuation is less than 100 µg; and
   wherein the dose provides a baseline-adjusted $FEV_1$ in a patient of more than 150 mL within 30 minutes of receiving the dose.

2. The inhaler as claimed in claim 1, wherein the baseline-adjusted $FEV_1$ remains above 150 mL for at least 6 hours after receiving the dose.

3. The inhaler as claimed in claim 1, wherein the dose of fluticasone propionate is less than 75 µg.

4. The inhaler as claimed in claim 3, wherein the doses of fluticasone propionate/salmeterol in µg are 50/12.75 or 25/12.75 per actuation.

5. The inhaler as claimed in claim 1, wherein the particle size of the fluticasone propionate is d10=0.4-1.1 µm, d50=11.1-3.0 µm, d90=2.6-7.5 µm and NLT95%<10 µm, measured by laser diffraction as an aqueous dispersion.

6. The inhaler as claimed in claim 1, wherein the particle size of the salmeterol xinafoate is d10=0.4-1.3 µm, d50=1.4-3.0 µm, d90=2.4-6.5 µm and NLT95%<10 µm, measured by laser diffraction as an aqueous dispersion.

7. The inhaler as claimed in claim 1, wherein the lactose carrier is comprised of a coarse lactose and fine lactose, wherein the fine lactose is defined by a particle size of <10 µm, measured by laser diffraction as a dispersion in air.

8. The inhaler as claimed in claim 7, wherein the lactose carrier contains 1-10 wt % of fine lactose.

9. The inhaler as claimed in claim 1, wherein the lactose particle size is d10=15-50 µm, d50=80-120 µm, d90=120-200 µm.

10. The inhaler as claimed in claim 1, wherein the inhaler comprises a cyclone deagglomerator for breaking up agglomerates of the dry powder.

11. The inhaler as claimed in claim 10, wherein the deagglomerator comprises:
    an inner wall defining a swirl chamber extending along an axis from a first end to a second end;
    a dry powder supply port in the first end of the swirl chamber for providing fluid communication between a dry powder delivery passageway of the inhaler and the first end of the swirl chamber;
    at least one inlet port in the inner wall of the swirl chamber adjacent to the first end of the swirl chamber providing fluid communication between a region exterior to the deagglomerator and the first end of the swirl chamber;
    an outlet port providing fluid communication between the second end of the swirl chamber and a region exterior to the deagglomerator; and
    vanes at the first end of the swirl chamber extending at least in part radially outwardly from the axis of the chamber, each of the vanes having an oblique surface facing at least in part in a direction transverse to the axis; whereby a breath induced low pressure at the outlet port causes air flows into the swirl chamber through the dry powder supply port and the inlet port.

12. The inhaler as claimed in claim 1, wherein the inhaler comprises a reservoir for containing the medicament and an arrangement for delivering a metered dose of the medicament from the reservoir.

13. The inhaler as claimed in claim 1, wherein the inhaler comprises a delivery passageway for directing an inhalation-induced air flow through a mouthpiece and a channel extending from the delivery passageway to the medicament.

14. The inhaler as claimed in claim 1, comprising:
    a sealed reservoir including a dispensing port;
    a channel communicating with the dispensing port and including a pressure relief port;
    a conduit providing fluid communication between an interior of the sealed reservoir and the pressure relief port of the channel; and
    a cup assembly movably received in the channel and including, a recess adapted to receive medicament when aligned with the dispensing port, a first sealing surface adapted to seal the dispensing port when the recess is unaligned with the dispensing port, and a second sealing surface adapted to sealing the pressure relief port when the recess is aligned with the dispensing port and unseal the pressure relief port when the recess is unaligned with the dispensing port.

15. The inhaler as claimed in claim 1 for the treatment of asthma or COPD.

16. The inhaler as claimed in claim 3, wherein the dose of fluticasone propionate/salmeterol in µg is 49/12.75 per actuation.

17. A method for the treatment of asthma or allergic rhinitis or COPD comprising administering to a patient a dry powder medicament comprising fluticasone propionate, salmeterol xinafoate and a lactose carrier; wherein, the delivered dose of fluticasone propionate per actuation is less than 100 µg; and wherein the dose provides a baseline-adjusted $FEV_1$ in a patient of more than 150 mL within 30 minutes of receiving the dose.

18. The method as claimed in claim 17, wherein the dose of fluticasone propionate is less than 75 µg.

19. The method as claimed in claim 17, wherein the doses of fluticasone propionate/salmeterol in μg are 50/12.75 or 25/12.75 per actuation.

20. The method as claimed in claim 17, wherein the dose of fluticasone propionate/salmeterol in μg is 49/12.75 per actuation.

* * * * *